United States Patent [19]

Weber et al.

[11] Patent Number: 5,429,934
[45] Date of Patent: Jul. 4, 1995

[54] PROCESS FOR THE PRODUCTION OF 20-METHYL-5,7-PREGNADIENE-3β,21-DIOL DERIVATIVES USING MYCOBACTERIUM

[75] Inventors: Alfred Weber; Mario Kennekke; Gunter Neef, all of Berlin, Germany

[73] Assignee: Schering Aktiengesellschaft, Berlin and Bergkamen, Germany

[21] Appl. No.: 861,809
[22] PCT Filed: Aug. 1, 1991
[86] PCT No.: PCT/DE91/00623
§ 371 Date: Jun. 18, 1992
§ 102(e) Date: Jun. 18, 1992
[87] PCT Pub. No.: WO92/03465
PCT Pub. Date: Mar. 5, 1992
[51] Int. Cl.$^6$ .................. C12P 33/00; C12N 1/20
[52] U.S. Cl. ............................ 435/52; 435/253.1; 435/53; 435/56; 552/586; 552/599; 552/600; 552/623
[58] Field of Search ............ 435/52, 253.1; 522/586, 522/599, 600, 623

[56] References Cited

U.S. PATENT DOCUMENTS

| | | | |
|---|---|---|---|
| 3,095,411 | 6/1963 | Kirk et al. | 552/600 |
| 3,983,111 | 9/1976 | Phillipps et al. | 552/586 |
| 4,150,126 | 4/1979 | Fea et al. | 552/599 |
| 4,214,052 | 7/1980 | Wovcha et al. | 435/55 |
| 4,252,716 | 2/1981 | Breslow et al. | 552/599 |
| 4,320,195 | 3/1982 | Hill et al. | 435/54 |
| 4,329,432 | 5/1982 | Knight et al. | 435/253.1 |
| 4,339,539 | 8/1982 | Wovcha et al. | 435/253.1 |
| 4,429,041 | 1/1984 | Wovcha et al. | 435/253.1 |
| 5,166,055 | 11/1992 | Slijkhuis | 435/253.1 |

FOREIGN PATENT DOCUMENTS

| | | |
|---|---|---|
| 0045524 | 2/1982 | European Pat. Off. . |
| 0377743 | 7/1990 | European Pat. Off. . |
| 2250864 | 10/1990 | Japan . |
| 2250865 | 10/1990 | Japan . |
| 8800988 | 1/1990 | WIPO . |

OTHER PUBLICATIONS

Chemical Abstracts, vol. 98, 1983 (98:16936u).
Takayama et al., "Facile, Stereoselective Synthesis of (24R)-24,25-Dihydroxyvitamin D", Tetrahedron Letters, vol. 21, pp. 5027-5028 (1980).
Reg File No. 132705-08.9.
Reg File No. 126771-89-9.
Reg File No. 103656-29-7.

*Primary Examiner*—Douglas W. Robinson
*Assistant Examiner*—Jeffrey J. Sevigny
*Attorney, Agent, or Firm*—Millen, White, Zelano, & Branigan

[57] ABSTRACT

20-Methyl-5,7-pregnadiene-3β,21-diol derivatives of general formula I

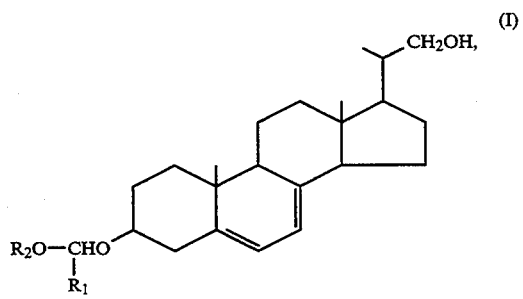

in which
$R_1$ means a hydrogen atom or a lower alkyl group and
$R_2$ means a lower alkyl group or
$R_1$ and $R_2$ together represent a tetramethylene group or a pentamethylene group and a process for their production are described.

1 Claim, No Drawings

PROCESS FOR THE PRODUCTION OF 20-METHYL-5,7-PREGNADIENE-3β,21-DIOL DERIVATIVES USING MYCOBACTERIUM

The invention relates to 20-methyl-5,7-pregnadiene-3β,21-diol derivatives of general formula I

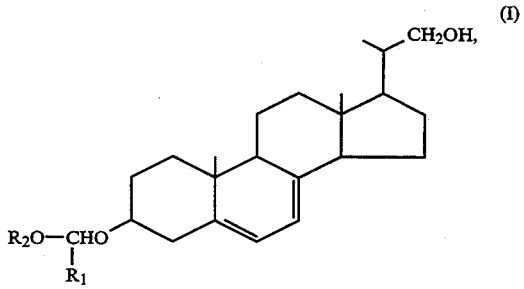

in which
R$_1$ means a hydrogen atom or a lower alkyl group and
R$_2$ means a lower alkyl group or
R$_1$ and R$_2$ together represent a tetramethylene group or a pentamethylene group.

The invention further relates to a process for the production of these 20-methyl-5,7-pregnadiene-3β,21-diol derivatives, which is characterized in that an ergosterol derivative of general formula II

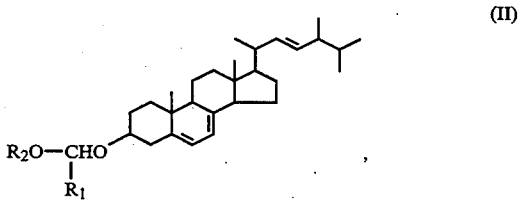

in which R$_1$ and R$_2$ have the meaning mentioned in claim 1, are fermented with a bacterial culture of genus Mycobacterium.

For fermentation, bacterial cultures of species Mycobacterium spec. NRRL B-3683, Mycobacterium spec. NRRL B-3805, Mycobacterium phlei NRRL B-8154 mycobacterium fortuitum NRRL B-8153 are preferably used.

It is very surprising to one skilled in the art that the 20-methyl-5,7-pregnadiene-3β,21-diol derivatives of general formula I are formed under the conditions of the process according to the invention, since it is known that other sterol-3-acetals are catabolized to 17-oxosteroids under these conditions (U.S. Pat. No. 4,179,336).

The process according to the invention is performed under the same fermentation conditions which are also used with these bacterial cultures in the known microbiological conversions of substrates.

Under the culture conditions usually used for these bacterial cultures, submerged cultures are cultivated in a suitable nutrient medium with aeration. Then, the substrate (dissolved in a suitable solvent or in emulsified form) is added to the cultures and fermented until a maximum substrate conversion is achieved.

Suitable substrate solvents are, for example, methanol, ethanol, glycol monomethyl ether, dimethylformamide or dimethylsulfoxide. The emulsification of the substrate can be brought about, for example, by the latter being sprayed in micronized form or dissolved in a water-miscible solvent (such as methanol, ethanol, acetone, glycol monomethyl ether, dimethylformamide or dimethylsulfoxide) under strong turbulence in (preferably decalcified) water, which contains the usual emulsifying aids. Suitable emulsifying aids are nonionogenic emulsifiers, such as, for example, ethylenoxy adducts or fatty acid esters of polyglycols. As suitable emulsifiers, the commercially available wetting agents Tegin$^{(R)}$, Tween$^{(R)}$ and Span$^{(R)}$ can be mentioned as examples.

The optimum substrate concentration, substrate addition time and fermentation period depend on the type of substrate and microorganism used and fermentation conditions. These values, as is generally necessary in microbiological steroid conversions, have to be determined in the individual case by preliminary tests, as they are familiar to one skilled in the art.

The 20-methyl-5,7-pregnadiene-3β,21-diol derivatives of general formula I produced according to the process of the invention are valuable intermediate products, which preferably can be used for the synthesis of vitamin D$_3$ and its derivatives. Thus, for example, these compounds can be esterified to the 21-tosylates and the latter can be reacted under the conditions which A. Fürst et al. have described (Helv. Chim. Acta 65, 1982, 1499–1521). Thus, compounds of general formula III

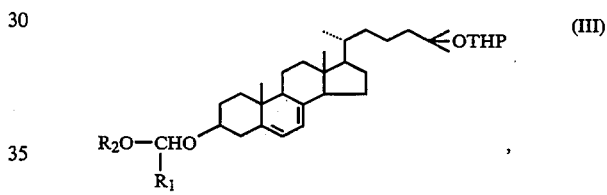

are obtained whose acetal groups are cleaved. The photochemical rearrangement of the thus obtained 25-hydroxy cholesterol in 25-hydroxy vitamin D$_3$ can also be performed according to the process, as was described by A. Fürst et al.

The initial compounds for the process according to the invention can be produced under the conditions described in U.S. Pat. No. 4,179,336.

The following embodiment is used to explain the process according to the invention in more detail.

EXAMPLE a) 400 g of ergosterol is dissolved in 6 l of formaldehyde dimethylacetyl, mixed with stirring at room temperature with 400 g of diatomaceous earth and in portions with 200 g of phosphorus pentoxide and stirred for 2 hours at room temperature. It is filtered off from insolubles, washed with formaldehyde dimethylacetal and the solvent is distilled off in a vacuum. After adding sodium bicarbonate solution, the solid crude product is filtered off, washed with water, and after drying, 440 g of 3β-methoxymethoxy-ergosta-5,7,22-triene is obtained.

b) A 2 l Erlenmeyer with 500 ml of sterile nutrient medium containing
1% yeast extract
0.45% Na$_2$HPO$_4$
0.34% KH$_2$PO$_4$
0.2% Tween 80
adjusted to pH 6.7 is inoculated with an elutriation of a dry culture of Mycobacterium spec. NRRL B-3805 and shaken for 3 days with 180 revolutions at 30° C.

c) 22.5 g of 3β-methoxymethoxy-ergosta-5,7,22-triene is emulsified with 4.4 g of tegin and 430 ml of water at 95° C. with an Ultra-Turrax (Jahnke & Kunkel company) for 25 minutes and then filled to 1000 g with water. The emulsion is sterilized for 20 minutes at 120° C.

d) A 500 ml Erlenmeyer with 100 ml of sterile nutrient medium containing 2.5% corn steep liquor
0.25% soybean flour
0.3% $(NH_4)_2HPO_4$
0.25% Tween 80
adjusted to pH 6.5 is inoculated with 5 ml of the Mycobacterium-spec.-growing culture. Then, 13.3 ml of the emulsion produced under b) (this corresponds to 0.3 g of 3β-methoxymethoxy-ergosta-5,7,22-triene) is added and fermented for 120 hours at 30° C. with shaking with 220 revolutions per minute.

After completion of the fermentation, the culture broth is extracted twice with 100 ml of methyl isobutyl ketone each. The combined extracts are then mixed with 11 g of activated carbon and filtered by a folded filter. The filtrate is then concentrated by evaporation in a rotary evaporator at 50° C. and chromatographed on aluminum oxide. After completion of chromatography, 48 mg of 3β-methoxymethoxy-20-methyl-5,7-pregnadien-21-ol, which is identical with an authentic sample according to HPLC, is obtained.

We claim:

1. A process for the production of a compound of formula I

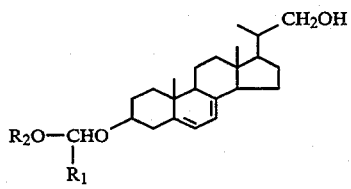

in which
$R_1$ is a hydrogen atom or a lower alkyl group and
$R_2$ is a lower alkyl group or
$R_1$ and $R_2$ together represent a tetramethylene group or a pentamethylene group comprising fermenting an ergosterol compound of formula II

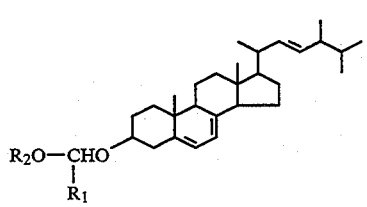

in which $R_1$ and $R_2$ have the above defined meanings with a bacterial culture selected from the group consisting of Mycobacterium spec. NRRL B-3683, Mycobacterium spec. NRRL B-3805, Mycobacterium phlei NRRL B-8154, and Mycobacterium fortuitum NRRL B-8153.

* * * * *